United States Patent [19]

Stephan

[11] 4,252,624

[45] Feb. 24, 1981

[54] BROMINATION OF M-ETHYLDIPHENYL ETHER

[75] Inventor: Erwin A. Stephan, Indianapolis, Ind.

[73] Assignee: Eli Lilly and Company, Indianapolis, Ind.

[21] Appl. No.: 32,839

[22] Filed: Apr. 24, 1979

[51] Int. Cl.³ .............................................. C07C 41/22
[52] U.S. Cl. ............................ 204/158 HA; 568/639; 260/465 H; 562/471
[58] Field of Search ................. 568/639; 204/158 HA

[56] References Cited

U.S. PATENT DOCUMENTS 4,085,147  4/1978  Rosinger et al. ................ 568/639 X

FOREIGN PATENT DOCUMENTS 2707232  8/1978  Fed. Rep. of Germany .

OTHER PUBLICATIONS

Kochergin et al., Chem. Abs., vol. 58 (1963), 8942(b).

Primary Examiner—Bernard Helfin
Attorney, Agent, or Firm—James L. Rowe; Arthur R. Whale

[57] ABSTRACT m-($\alpha$-Bromoethyl)diphenyl ether is prepared by a free radical bromination of m-ethyldiphenyl ether.

1 Claim, No Drawings

4,252,624

BROMINATION OF M-ETHYLDIPHENYL ETHER

BACKGROUND OF THE INVENTION m- and p-Substituted-α-phenylpropionic acids or phenylacetic acids, their salts, esters etc. are presently being marketed as anti-inflammatory agents or peripheral analgesics. Among these agents are ibuprofen, (±) α-methyl-4-(2-methylpropyl)benzeneacetic acid; carprofen, (±) α-6-chloro-α-methylcarbazole-2-acetic acid; cicloprofen, α-methylfluorene-2-acetic acid; fenoprofen, dl-α-methyl-3-phenoxybenzeneacetic acid; indoprofen, α-methyl-4-(1,3-dihydro-1-oxo-2H-isoindoyl-2-yl)benzeneacetic acid; ketoprofen, α-methyl-3-benzoylbenzeneacetic acid; naproxyn, (+) α-methyl-6-methoxy-2-naphthaleneacetic acid; pirprofen, dl-3-chloro-4-(2,5-dihydro-1H-pyrrolo-1-yl)-α-methylbenzeneacetic acid; suprofen, dl-α-methyl-4-(2-thienylcarbonyl)benzeneacetic acid and benzoxoprofen, dl-α-methyl-2-(p-chlorophenyl)benzoxazoleacetic acid. A common method of preparing these compounds is to start with an acetyl derivative, reduce the carbonyl group to a hydroxyl, replace the hydroxyl with a halogen, react the haloalkyl group with sodium cyanide to yield a propionitrile derivative and then hydrolyze the nitrile group to a carboxylic acid. Alternatively, a benzyl halide can be converted to the corresponding acetonitrile and the active methylene group methylated to yield directly the α-methyl acetontrile. Several of these methods are set forth in U.S. Pat. No. 3,600,437 which covers fenoprofen.

In general, the most desirable route for preparing any one of the above "profen" antiinflammatory agents depends primarily upon the availability of the starting material. For example, starting materials for the synthesis of fenoprofen can be selected from among m-bromoacetophenone, m-hydroxyacetophenone, m-bromophenylacetonitrile etc. In addition, certain of the side chain functional groups; i.e. hydroxy or carbonyl, affect the course of a reaction to replace the m-bromo or m-hydroxy group in the phenyl ring with a phenoxy or other group. Alternative methods for the preparation of any of the "profen" anti-inflammatory agents and particularly of fenoprofen are clearly desirable.

One of the synthetic routes available for the manufacture of benoxaprofen is set forth in U.S. Pat. No. 3,912,748 (also U.S. Pat. No. Re 29,608) both based on a British provisional application No. 23409/72 filed May 18, 1972. This procedure involves nitration of p-ethylphenol followed by acylation of the phenolic group by p-chlorobenzoyl chloride and cyclization of the acylated phenol. The resulting compound, 2-(p-chlorophenyl)-5-ethylbenzoxazole, is brominated by a free radical mechanism on the alpha carbon of the ethyl side chain to yield α-methyl-2-(p-chlorophenyl)-5-benzoxazolylmethylbromide a compound also used in the standard synthesis of benoxaprofen and a compound which can be readily converted to the corresponding nitrile and thence to the acid followed by cyclization. Free radical bromination steps are clearly not useful for the synthesis of all "profen" anti-inflammatory agents since there may be other groups in the molecule which could also react with bromine by a free radical mechanism. For example, in a comparable synthesis of ibuprofen, the compound to be brominated would be p-isobutylethylbenzene in which either alkyl group would react with a free bromine radical.

A recent West German OLS No. 2,707,232 of Aug. 24, 1978, filed Feb. 19, 1977, discloses and claims a method for preparing m-phenoxybenzyl bromides or chlorides in which the carbon to be halogenated can also be substituted by another halogen, or an alkyl, aryl, $C_1$-$C_4$ haloalkyl, alkoxycarbonyl, cyano or nitro group. A free radical bromination is employed.

It is an object of this invention to provide a process for the preparation of fenoprofen in good yield and of excellent purity starting with m-ethylphenol. It is a further object of this invention to provide a method of brominating m-ethyldiphenyl ether in high yield.

DESCRIPTION OF THE INVENTION

This invention provides a method for the preparation of fenoprofen starting with m-ethylphenol. The method is outlined in Reaction Scheme I below.

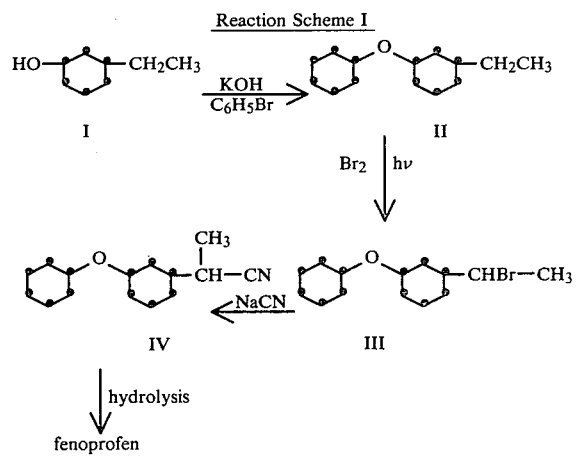

In the above reaction scheme, m-ethylphenol (I) is treated at high temperature with bromobenzene in the presence of potassium hydroxide and preferrably in the presence of a catalytic quantity of cuprous chloride, copper powder or copper bronze powder. The reaction conditions are those of the Ullmann modification of the standard Williamson ether synthesis [see *Ber.*, 38, 2211 (1905); *Ann.*, 350, 86 (1906); see also Bacon and Stuart, *J. C. S.* (London) 4953 (1965) for reaction conditions]. The product of this reaction, m-ethyldiphenyl ether (II), is then treated with bromine preferably in a mutual inert solvent in the presence of light or a chemical free radical initiator. The bromine attacks the 2-ethyldiphenyl ether by a free radical mechanism and displaces one of the aliphatic hydrogens on the α-carbon of the ethyl side chain rather than one of the aromatic hydrogens in the phenyl rings. The product of this reaction is m-(α-bromoethyl)diphenyl ether (III). This intermediate is a common intermediate for the preparation of fenoprofen, being disclosed in U.S. Pat. No. 3,600,437 column 14 line 10 et seq. Conversion of this bromide to 2-(3-phenoxyphenyl)-propionitrile and hydrolysis of the nitrile to yield the corresponding acid are also fully set forth in U.S. Pat. No. 3,600,437 column 14 lines 28-64.

In Reaction Scheme I, the yield of m-ethyldiphenyl ether (II) is 96% based upon recovered m-ethylphenol. The Ullman ether synthesis proceeds more readily and gives a higher yield when applied to the reaction of bromobenzene and m-ethylphenol than when applied to a comparable reaction step in the standard fenoprofen synthesis between m-bromoacetophenone and potassium phenoxide. m-Ethylphenol, bromobenzene and the resulting m-ethyldiphenylether are more stable under the high temperature (200° C. and above) and extremely alkaline reaction conditions of the Ullman ether synthesis than are m-bromoacetophenone or m-acetyldiphenyl ether.

The intermediate α-bromo-m-ethyldiphenyl ether is usually not isolated but converted directly to the propionitrile (IV) by treatment with NaCN. The yield of propionitrile based on recovered m-ethyldiphenyl ether is 82% or higher.

In carrying out the step of the above reaction involving bromination of the ethyl side chain, (II→III) it is important that the amount of bromine be carefully controlled. In fact, better yields are obtained when a less than theoretical quantity of bromine (about 10% below theory) is employed. The use of less than stoichiometric amounts of bromine minimizes ring bromination as well as further bromination of the side chain of either a ring brominated or side chain brominated compound. In carrying out the bromination, a free radical initiator must be employed. Such a free radical initiator can be a chemical compound such as "azobis" (azobisisobutyronitrile) or it can be ultraviolet light. I have used successfully mercury vapor lamps, fluorescent lamps and sun lamps each having a component radiation in the UV. The lamp is ordinarily employed in a quartz or pyrex (non-opaque to ultraviolet light) apparatus. The following examples illustrate the preparation of m-(α-bromoethyl)diphenyl ether (α-methyl-3-phenoxybenzyl bromide).

EXAMPLE 1

A reaction mixture was prepared by dissolving 99 g. of m-ethyldiphenyl ether in 300 ml. of benzene at the reflux temperature of benzene in a pyrex reaction vessel. A 275 watt sun lamp was placed about 6 inches from the reaction vessel. The sun lamp was turned on and a solution of 29.1 ml. of bromine in 75 ml. of benzene was added by dropwise addition over a 2.5 hour period. The bromine reacted rapidly as evidenced by rapid disappearance of the bromine color. At the conclusion of the run, an analysis of the reaction mixture indicated that only 5.6% of m-ethyldiphenyl ether had not reacted. The reaction was worked up by washing the benzene solution twice with 2% aqueous sodium bicarbonate and concentrating the residual benzene solution at 50° C. to dryness. About 100 ml. of product was obtained.

A reaction mixture was prepared with 375 ml. of water 33.2 g. of sodium cyanide and 330 ml. of DMF. This mixture was heated at 50° C. At this point m-(α-bromoethyl)diphenyl ether prepared as above was added in dropwise fashion over a 1.5 hour period. An analysis of the reaction mixture indicated that, after four hours, over 80% of the bromide had been converted to the corresponding nitrile.

A similar bromination reaction to that set forth above can be produced by using 0.4% added "azobis" in place of an external light source.

A similar bromination was carried out employing chloroform in place of benzene as the solvent. A yield of about 90% of desired bromo compound was obtained and about 10% recovered starting material.

EXAMPLE 2

Sixty kg. of m-ethyldiphenyl ether were dissolved in 425 l. of benzene and the solution extracted five times with 120 liter portions of 5% aqueous sodium hydroxide followed by two water extractions of 120 liters each followed by two 120 liter washes with 10% aqueous hydrochloric acid and finally by a a single 120 liter water wash. The benzene layer containing the m-ethyldiphenyl ether from which any residual phenol had been extracted by the above procedure was washed into a reactor with 50 liters of benzene. Sixty liters of water were added and the mixture heated to a temperature in the range 70°-75° C. at which temperature it was held for 30 minutes. A 100 watt mercury vapor lamp in a side arm of the reaction vessel was turned on. A solution of 50.4 kg. of bromine in 60 l. of benzene was added at the rate of 500-600 grams per minute. After about 48 kg. of bromine had been added, the color of the solution no longer discharged rapidly, indicating that the reaction was substantially complete. All of the bromine was added, however, and the reaction mixture heated at reflux temperature for an additional 15 minutes after which time it was cooled and the aqueous layer separated. The benzene layer was extracted twice with 120 liters portions of water after which the benzene was removed therefrom by evaporation at a temperature below about 40° C. The residue, comprising m-(1-bromoethyl)phenyl phenyl ether was then added to a second reactor that contained 250 liters of DMF, 18 liters of water and 16.7 kg. of sodium cyanide. This mixture had been thoroughly stirred and cooled to about 15° C. before addition of the m-(1-bromoethyl)-phenyl phenyl ether. An additional 20 liters of DMF were used to rinse in the diphenyl ether. The reaction mixture was heated slowly to about 50° C. until the reaction was completed. 300 l. of DMF were removed by distillation and 140 liters of toluene plus 140 liters of water added to the reaction vessel. The aqueous layer was separated and the organic layer washed with 140 l. of water. The organic solvent was removed by evaporation. The resulting residue weighed 66.5 kg., 77% of which was α-methyl-3-phenoxybenzeneacetonitrile. The cyanide was purified by standard procedures.

I claim:

1. In the process for preparing m-(α-bromoethyl)-diphenyl ether by the free radical bromination of m-ethyldiphenyl ether with bromine in the presence of a free radical initiator in a mutual inert solvent, the improvement which comprises carrying out the reaction in the presence of water and utilizing less than one mole of molecular bromine per mole of m-ethyldiphenyl ether.

* * * * *